(12) United States Patent
Treves et al.

(10) Patent No.: US 6,566,674 B1
(45) Date of Patent: May 20, 2003

(54) METHOD AND APPARATUS FOR INSPECTING SUBSTRATES

(75) Inventors: David Treves, Palo Alto, CA (US); Thomas A. O'Dell, Campbell, CA (US); Yung-Chieh Hsieh, San Jose, CA (US)

(73) Assignee: Komag, Inc., San Jose, CA (US)

( * ) Notice: Subject to any disclaimer, the term of this patent is extended or adjusted under 35 U.S.C. 154(b) by 0 days.

(21) Appl. No.: 09/337,709

(22) Filed: Jun. 21, 1999

(51) Int. Cl.$^7$ ............................................... G01N 21/88
(52) U.S. Cl. ................................................ 250/559.46
(58) Field of Search ................. 250/559.45, 559.46, 250/559.48, 559.49

(56) References Cited

U.S. PATENT DOCUMENTS

| | | | |
|---|---|---|---|
| 3,679,307 A | * 7/1972 | Zoot et al. ..................... 356/4 |
| 3,999,865 A | 12/1976 | Milam et al. ................ 356/239 |
| 4,065,786 A | 12/1977 | Stewart ....................... 358/128 |
| 4,092,068 A | 5/1978 | Lucas et al. ................... 356/73 |
| 4,355,904 A | 10/1982 | Balasubramanian ........ 356/376 |
| 4,395,122 A | 7/1983 | Southgate et al. ........... 356/237 |
| 4,402,607 A | 9/1983 | McVay et al. ............... 356/339 |
| 4,412,743 A | 11/1983 | Eberly ......................... 356/237 |
| 4,544,241 A | * 10/1985 | LaBudde et al. ............ 350/486 |
| 4,600,996 A | 7/1986 | Kawauchi .................... 364/491 |
| 4,627,724 A | 12/1986 | Cameron ..................... 356/141 |

(List continued on next page.)

FOREIGN PATENT DOCUMENTS

| | | |
|---|---|---|
| EP | 0 793 092 | 9/1997 |
| JP | 50-80123 | 6/1975 |
| JP | 3-214423 | 9/1991 |
| JP | 5-56459 | 3/1993 |
| JP | 8-14868 | 1/1996 |
| JP | 8-128965 | 5/1996 |
| JP | 9-26396 | 1/1997 |
| JP | 9-33446 | 2/1997 |
| JP | 10-134443 | 5/1998 |
| JP | 10-143801 | 5/1998 |
| JP | 10-260012 | 9/1998 |
| WO | WO 97/27467 | 7/1997 |
| WO | WO 98/44330 | 10/1998 |

OTHER PUBLICATIONS

Vlasta Cejna, et al., "Design and Application of Optical Defect Detection Systems in the Production Process", Phase Metrics located in San Diego, California (total of four pages, pages unnumbered).
Dialog Printout regarding Japanese reference 5–56459, which reference was published in 1993.
Silicon Photodiodes 1994 Catalog published by Centronic of Newbury Park, California, pp. 1, 2, 13–15 and 31–38.
Optoelectronic Components Catalog, published by UDT Sensors, Inc. of Hawthorne, California, pp. and 28–37.
Optoelectronics DataBook, published by Advanced Photonicx, Inc. of Camarillo, California pp. 32–35.
Silicon Photodiodes 1994 Catalog published by Centronic.
Optoelectronic Components Catalog, published by UDT Sensors, Inc.
Otoelectronics DataBook, published by Advanced Photonicx, Inc.
Vlasta Cejna, et al., "Design and Application of Optical Defect Detection Systems in the Production Process".

Primary Examiner—Michael P. Stafira
Assistant Examiner—Andrew H. Lee

(57) ABSTRACT

Apparatus for detecting defects in a substrate comprises a laser for providing a laser beam, and a bi-cell photodiode comprising two cells. Circuitry coupled to the bi-cell photodiode provides a signal equal to (L−R)/(L+R), where L and R equal the signal strengths of the signals provided by the left and right photodiode cells, respectively. The photodiode is biased so that it exhibits reduced capacitance, and can provide increased output signal bandwidth.

30 Claims, 7 Drawing Sheets

U.S. PATENT DOCUMENTS

| | | | |
|---|---|---|---|
| 4,629,319 A | 12/1986 | Clarke et al. | 356/237 |
| 4,766,512 A | 8/1988 | Bogdanski | 360/137 |
| 4,794,264 A | 12/1988 | Quackenbos et al. | 250/563 |
| 4,794,265 A | 12/1988 | Quackenbos et al. | 250/572 |
| 4,920,385 A * | 4/1990 | Clarke et al. | 356/237 |
| 4,933,552 A | 6/1990 | Lee | 250/310 |
| 4,943,734 A | 7/1990 | Johnson et al. | 250/572 |
| 5,153,844 A | 10/1992 | Beni et al. | 364/560 |
| 5,155,371 A | 10/1992 | Burggraf et al. | 250/563 |
| 5,189,481 A | 2/1993 | Jann et al. | 356/73 |
| 5,212,677 A | 5/1993 | Shimote et al. | 369/58 |
| 5,377,001 A | 12/1994 | Malin et al. | 356/237 |
| 5,377,002 A | 12/1994 | Malin et al. | 356/237 |
| 5,389,794 A * | 2/1995 | Allen et al. | 250/559.48 |
| 5,428,452 A | 6/1995 | Grycewicz | 356/430 |
| 5,602,639 A | 2/1997 | Kohno | 356/237 |
| 5,644,400 A | 7/1997 | Mundt | 356/400 |
| 5,661,559 A | 8/1997 | Brezoczky et al. | 356/353 |
| 5,719,840 A | 2/1998 | Jann | 369/58 |
| 5,781,649 A | 7/1998 | Brezoczky | 382/108 |
| 5,818,592 A | 10/1998 | Womack et al. | 356/357 |

\* cited by examiner

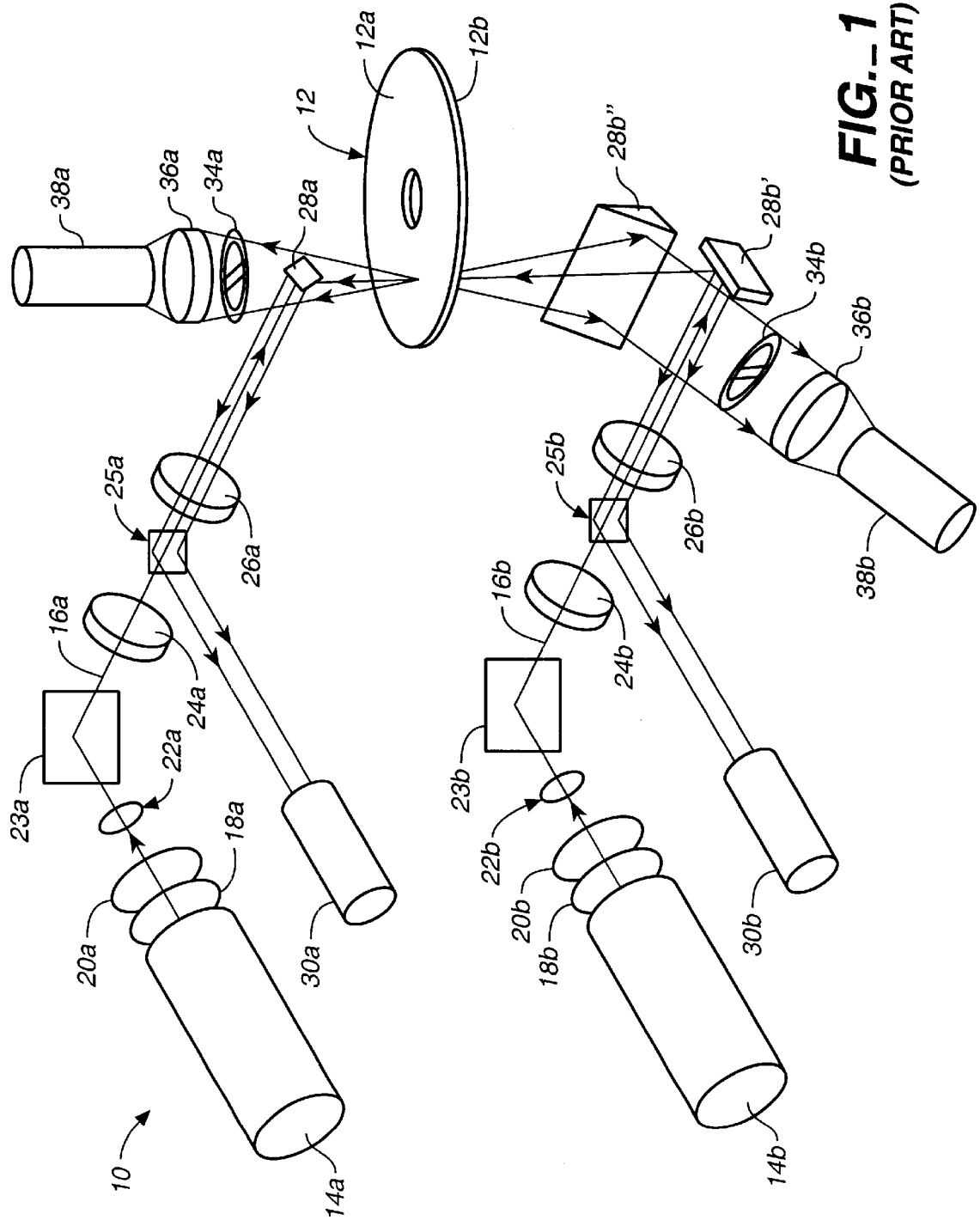
FIG._1 (PRIOR ART)

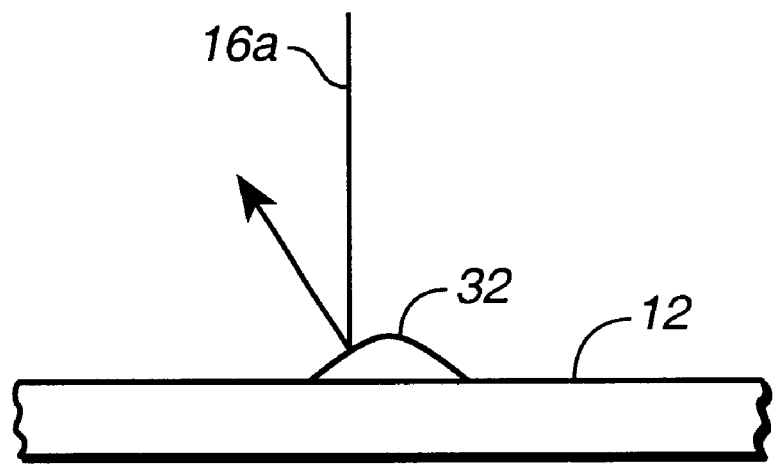
FIG._2A
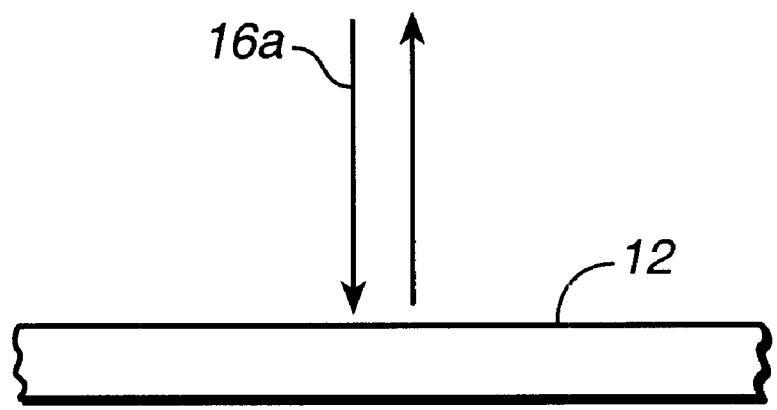
FIG._2B

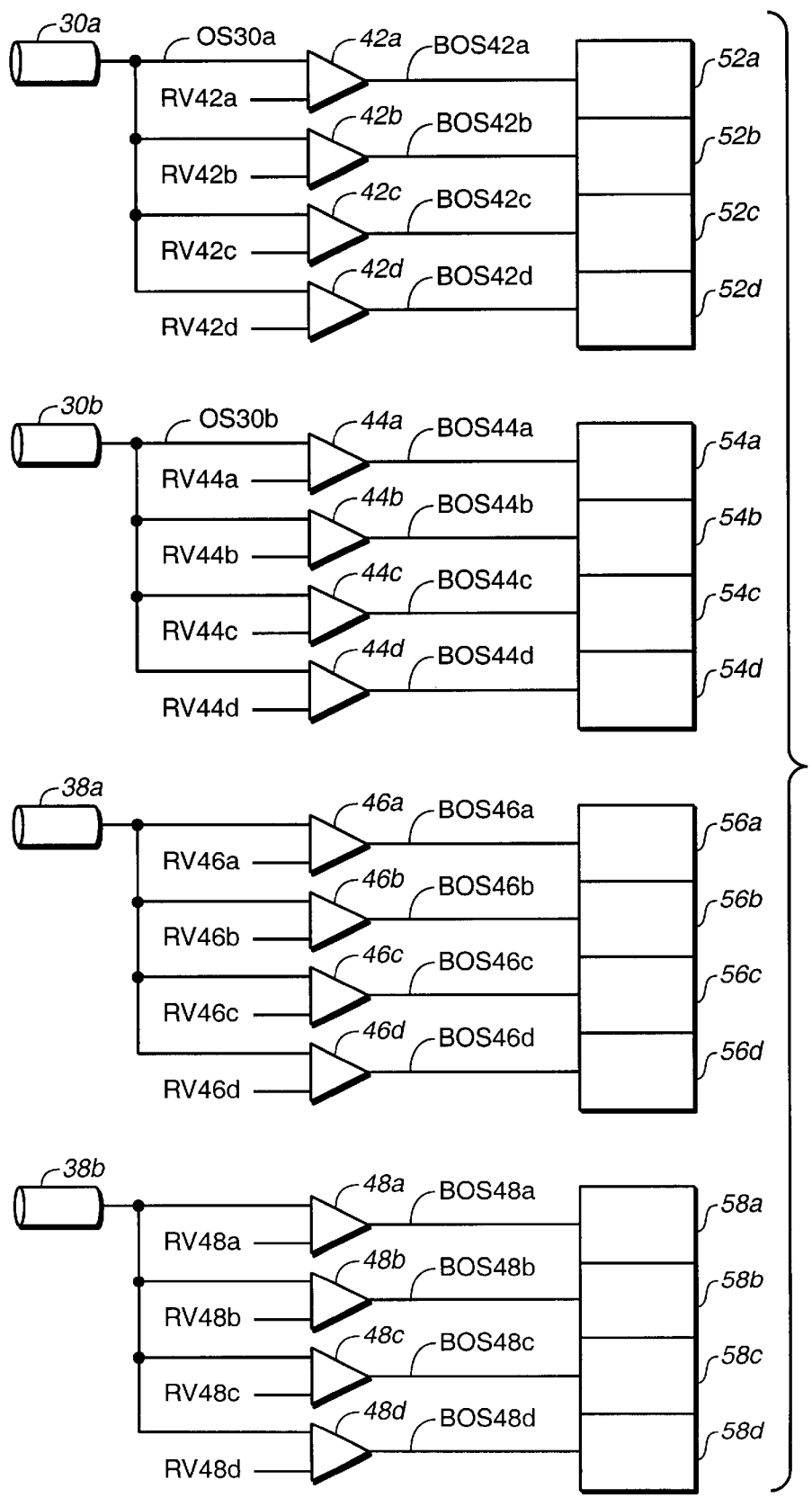
FIG._3
*(PRIOR ART)*

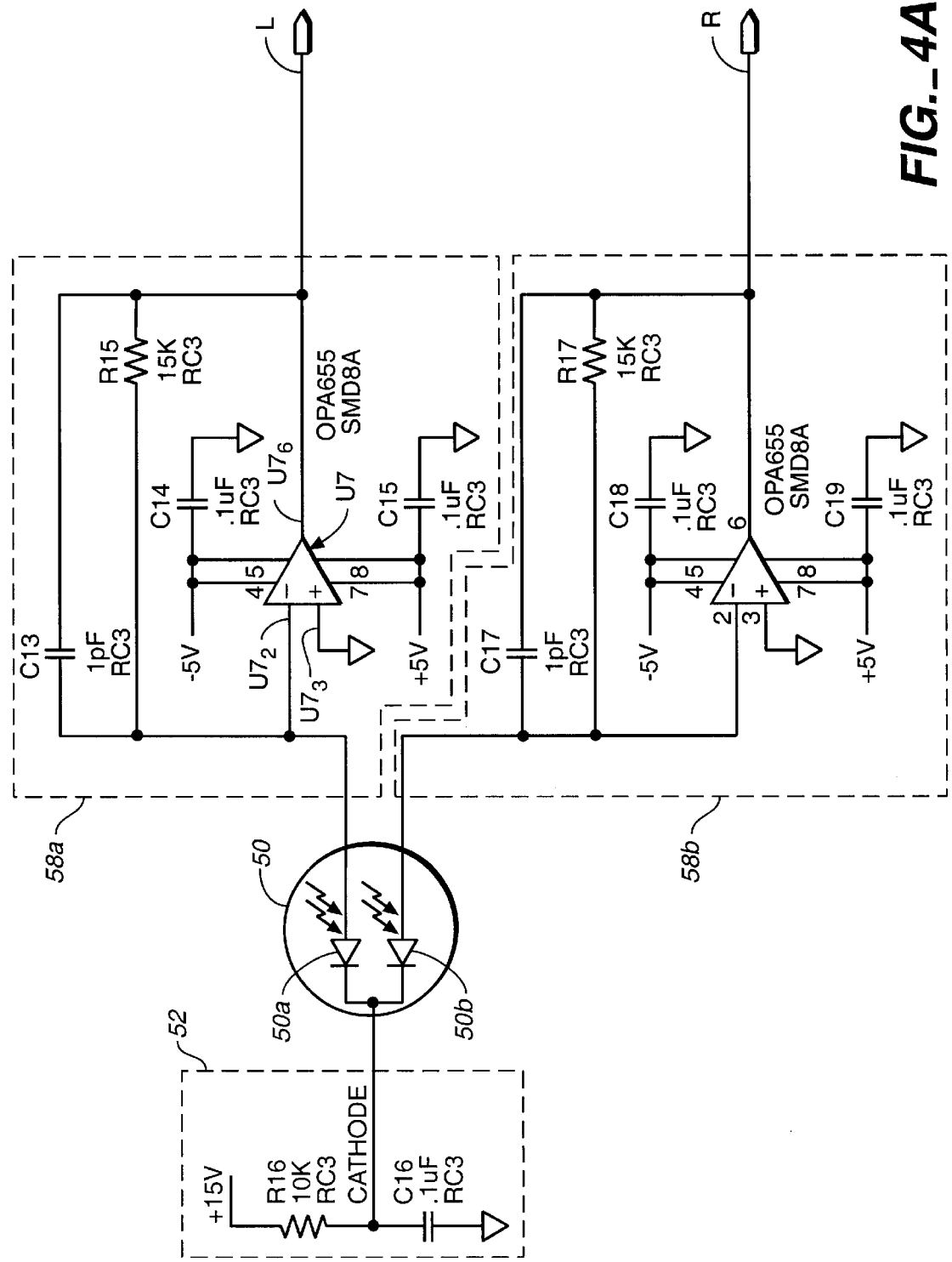
FIG._4A

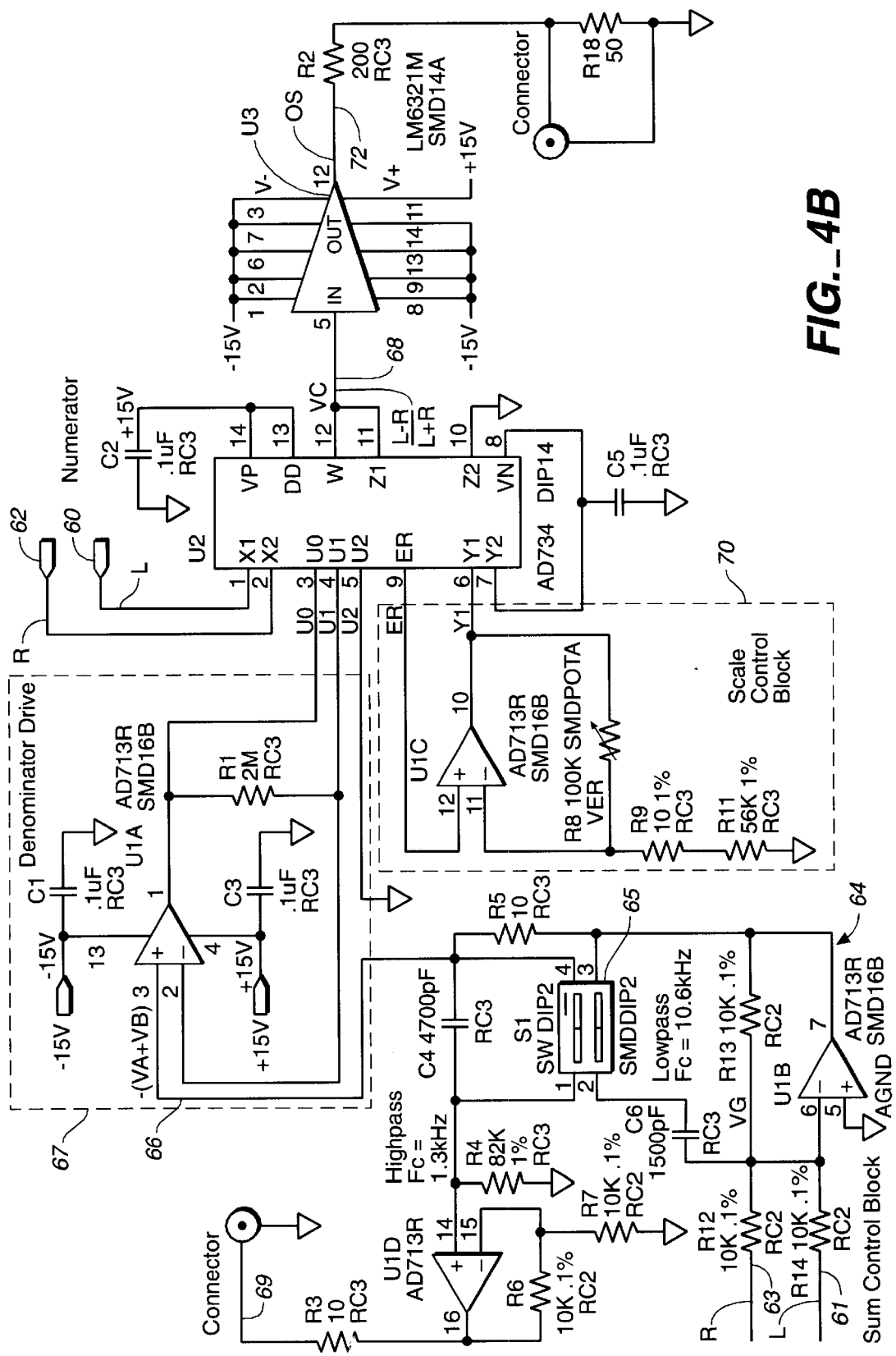
FIG._4B

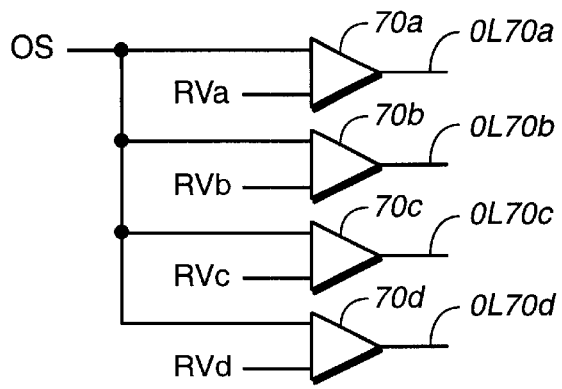
FIG._4C
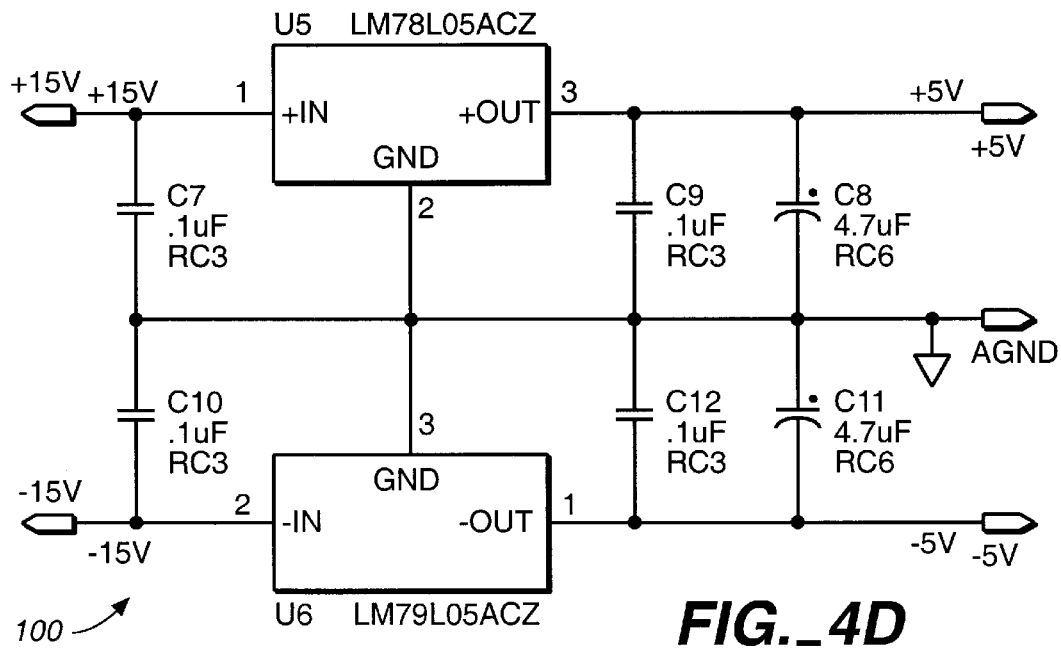
FIG._4D
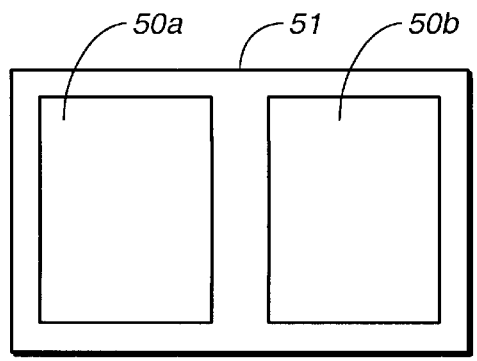
FIG._5

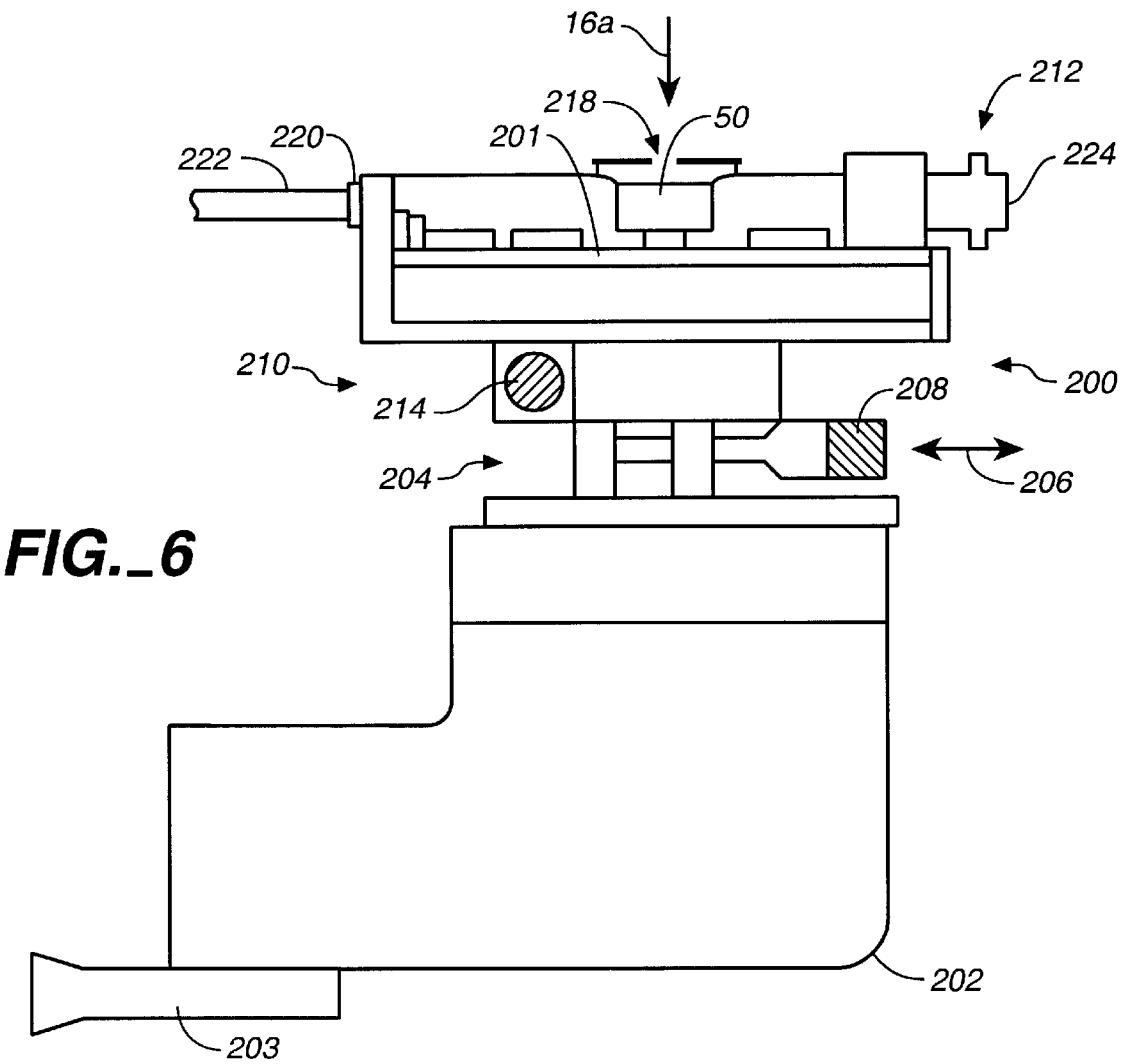
FIG._6

METHOD AND APPARATUS FOR INSPECTING SUBSTRATES

BACKGROUND OF THE INVENTION

This invention pertains to a method and apparatus for inspecting substrates used during the manufacture of magnetic disks.

Magnetic disks are typically manufactured by the following process:
1. An aluminum alloy substrate is electroless plated with NiP.
2. The plated substrate is polished.
3. The polished substrate is then textured, either mechanically or using a laser.
4 An underlayer (e.g. Cr or NiP), a magnetic alloy (typically a Co alloy) and a protective overcoat (typically carbon, hydrogenated carbon, or zirconia) are then sputtered, in that order, onto the substrate.
5. A lubricant is then applied to the protective overcoat.

The layers formed on magnetic disks (e.g. the underlayer, magnetic layer and overcoat) are extremely thin, e.g. on the scale of several tens of nanometers. It is very important that there be no or few large defects in the substrate prior to sputtering.

It is known in the art to use laser scanning systems to inspect magnetic disk substrates prior to sputtering. Examples of such systems include the PMT Pit Detector, the Diskan 6000, Diskan 9000 and Diskan 9001 systems manufactured by QC Optics of Burlington, Mass. Other prior art systems are discussed in U.S. Pat. Nos. 4,794,264; 4,794,265; and 5,389,794, each assigned to QC Optics.

FIG. 1 schematically illustrates a QC Optics Diskan 9001 apparatus 10 for detecting defects in a substrate, such as a substrate 12. Referring to FIG. 1, apparatus 10 comprises HeNe lasers 14a, 14b for generating laser beams 16a, 16b respectively. Laser beam 16a is used to scan across and inspect one side of substrate 12, while laser beam 16b is used to scan across and inspect the other side of substrate 12. (Substrate 12 is typically rotated by a motor during this inspection, and laser beams 16a, 16b typically scan in the radial direction of the substrate.)

Laser beam 16a passes through a polarizer 18a, ¼ waveplate 20a, and a shutter 22a, reflects off a mirror 23a, passes through a lens 24a, a beam splitter 25a, and a lens 26a and reflects off of mirror 28a. Mirror 28a deflects laser beam 16a downward to substrate 12. Substrate 12 reflects laser beam 16a upwardly and back to mirror 28a, through lens 26a and back to beam splitter 25a. Beam splitter 25a deflects laser beam 16b to a photomultiplier tube 30a. Of importance, if laser beam 16a strikes a defect in substrate 12 (either a pit or a bump), that defect will reflect laser beam 16a at an angle. The fact that laser beam 16a is reflected at an angle is detected by photomultiplier tube 30a. In this way, apparatus 10 can use laser beam 16a to determine whether there are pits or bumps in substrate 12.

The manner in which a defect deflects a laser beam can best be understood by comparing FIGS. 2A and 2B. In FIG. 2A, laser beam 16a strikes a portion of substrate 12 where defect 32 deflects laser beam 16a at an angle θ. In contrast, in FIG. 2B, laser beam 16b strikes a portion of substrate 12 where there are no defects. Thus, in FIG. 2B, laser beam 16a reflects straight back, and not at an angle. As mentioned above, photomultiplier tube 30a detects whether or not laser beam 16a is reflected at an angle by a defect on substrate 12.

Referring back to FIG. 1, portions of laser beam 16a are also reflected past mirror 28a, pass through spacial filter 34a and lens 36a, and strike photomultiplier tube 38a. (Spacial filter 34a filters out light scattering caused by the texture pattern that is formed on substrate 12.) Of importance, photomultiplier tube 38a determines whether light is scattered by defects or contamination on substrate 12 at a wide angle.

The optical path for laser beam 16b is similar to the optical path of laser beam 16a, and will not be described in detail, except to note that it includes two mirrors 28b' and 28b" instead of single mirror 28a.

FIG. 3 is a block diagram of the circuitry coupled to photomultiplier tubes 30a, 30b, 38a and 38b. As can be seen, each of photomultiplier tubes 30a, 30b, 38a and 38b is coupled to four comparators 42a–42d, 44a–44d, 46a–46d and 48a–48d, respectively. Each of comparators 42a–42d compares the output signal OS30a of photomultiplier tube 30a with an associated reference voltage RV42a–RV42d, and provides a binary output signal BOS42a–BOS42d in response thereto. Binary output signals BOS42a–BOS42d are stored in associated latches 52a–52d, the contents of which are loaded into a memory which can then be accessed by a central processing unit CPU (not shown). Comparators 44–48 similarly compare the output signals from photomultiplier tubes 30b, 38a and 38b to reference voltage signals RV, and generate binary output signals BOS in response thereto. These binary output signals are stored in latches 54–58, the contents of which can be accessed by central processing unit CPU to determine the size and character of a defect detected by the apparatus.

While apparatus 10 can detect some defects, it would be desirable to provide improved means for detecting such defects with greater sensitivity and accuracy.

SUMMARY

A method for inspecting a substrate in accordance with our invention comprises the step of providing a laser beam that strikes and reflects off the substrate and then strikes a bi-cell photodetector. In one embodiment, the photodetector is a photodiode. The cells of the photodetector are coupled to circuitry that generates a signal equal to (L−R), where L is the strength of the signal provided by one cell of the photodetector, and R is the strength of the signal provided by the other cell of the photodetector. The signal L−R corresponds to the difference between the amount of light striking one cell of the photodetector and the amount of light striking the other cell, which in turn depends on the extent to which the laser beam is deflected by a defect. A signal equal to L+R is also developed. Signal L+R is used to "normalize" signal L−R. In other words, signal L+R is used to compensate for sources of common mode noise, e.g. fluctuations in the intensity of the laser, variations in substrate reflectivity, etc. From these two signals, a signal proportional or equal to (L−R)/(L+R) is developed. Signal (L−R)/(L+R) is compared to a set of threshold circuits to determine the size of the defect detected.

In one embodiment, the bi-cell photodetector contains two photodiodes that are biased with a bias voltage so that the photodiodes exhibit reduced capacitance. Because of this, the circuit employing the bi-cell photodetector exhibits enhanced bandwidth, thereby improving the speed at which the substrate can be inspected.

We have found that one embodiment of apparatus in accordance with our invention is more sensitive to defects than the apparatus of FIG. 3. For example, the apparatus of FIG. 3 was capable of detecting defects having a wall slope of about 0.05° or greater. One embodiment of our invention can detect defects having a wall slope less than 0.02°, and in one embodiment, defects having a wall slope as low as 0.005°. (A defect wall slope of 0.005° typically represents the lower limit of presently feasible substrate manufacturing processes. If one could manufacture a flatter substrate, we believe the apparatus of the present invention could detect defects having wall slopes as low as 0.003°.)

BRIEF DESCRIPTION OF THE DRAWINGS

FIG. 1 schematically illustrates an optical system using a laser beam to inspect a substrate for defects constructed in accordance with the prior art.

FIG. 2A illustrates a laser beam striking a defect on a substrate.

FIG. 2B illustrates a laser beam striking a portion of a substrate that does not contain a defect.

FIG. 3 is a block diagram of a prior art circuit for processing a signal from a set of photomultiplier tubes within apparatus 10 of FIG. 1.

FIGS. 4A to 4D are a schematic diagram of a circuit for processing a signal from a light sensing diode in accordance with our invention.

FIG. 5 illustrates in plan view a bi-cell photodiode used in the circuit of FIGS. 4A to 4C.

FIG. 6 illustrates a module containing some of the circuitry of FIGS. 4A to 4D.

DETAILED DESCRIPTION

One embodiment of our invention uses most of the optical elements shown in FIG. 1. However, instead of using photomultiplier tubes 30 and the circuitry of FIG. 3, we have developed a new structure for detecting reflected laser beams 16 and generating an output signal to determine whether a defect is present on substrate 12. Specifically, instead of using photomultiplier 30a, a bi-cell photosensitive diode 50 is used (FIGS. 4A and 5). Bi-cell photosensitive diode 50 comprises a diode 50a and a diode 50b. Diodes 50a and 50b are roughly rectangular, and are formed on a common substrate 51 adjacent to one another, as shown in FIG. 5. In one embodiment, bi-cell photosensitive diode 50 is device model number SPOT-2D, manufactured by UDT of Hawthorne, Calif. In another embodiment, bi-cell photosensitive diode 50 is device number SD 113-24-21-021, manufactured by Advanced Photonics of Camarillo, Calif. However, other types of photosensitive diodes, photosensitive transistors, or other devices may also be used.

FIGS. 4A to 4C schematically illustrate circuitry for processing the output signal of diodes 50a, 50b. This circuitry comprises numerous components, e.g. resistors, capacitors, and various integrated circuits. The value of these components, and the part number of these integrated circuits are set forth in Table I below.

Referring to FIG. 4A, the cathode of diodes 50a, 50b are connected to a bias circuit 52 comprising a resistor R16 connected to a 15 volt source, and a capacitor C16 connected to ground. The anode of diode 52a is coupled to a preamplifier 58a for generating signal R. Similarly, the anode of diode 52b is coupled to a preamplifier 58b for generating signal L. Signals L and R are voltages representing the amount of light striking diodes 50a and 50b, respectively.

Preamplifier 58a comprises an operational amplifier U7 having an inverting input lead $U7_2$ coupled to diode 50a and a non-inverting input lead $U7_3$ connected to ground. Output lead $U7_6$ is coupled to input lead $U7_2$ via resistor R15 (typically 15 kΩ). Of importance, because of the manner in which diode 50a is biased, it exhibits a low capacitance. (All diodes exhibit a certain amount of capacitance due to their pn junctions.) The capacitance exhibited by diode 50a depends upon the bias voltage applied across it. By applying a relatively large voltage across photodiode 50a, we can ensure that the capacitance of diode 50a is relatively low, e.g. below 13 pF. (For example, in one embodiment, the capacitance of diode 50a is between 0.1 and 13 pF. For example, the capacitance can be between 3 and 13 pF.) The capacitance of diode 50a and resistor R15 form an RC filter. By ensuring that the capacitance of diode 50a is low, the time constant of this RC filter will be low, enabling preamplifier 58 to provide a signal having a bandwidth of at least 100 kHz. (The bandwidth typically exceeds 200 kHz, and can be between 500 kHz and 100 MHz. For example, in one embodiment, the bandwidth is about 10 MHz.) This bandwidth increases the speed at which the apparatus can inspect a substrate for defects.

Signal L is provided at input leads 60 and 61, and signal R is provided at input leads 62 and 63 of the circuitry of FIG. 4B. As explained below, this circuitry provides an output signal OS, indicative of defects on substrate 12.

Of importance, if there is no defect present on substrate 12, the same amount of light should strike diodes 52a and 52b, and signals L and R should be equal. If there is a defect present on substrate 12, laser beam 16a will be deflected in one direction or another (left or right), and one of signals L, R will be greater than the other signal R, L. As explained below, the circuitry of FIG. 4B provides a signal that is a measure of the difference between signals L and R. This signal is related to the extent to which a defect in substrate 12 deflects light to the left or right when it bounces off the defect.

Of importance, the amount of light provided by laser 14 (FIG. 1) can vary, thereby injecting noise into signals L and R. Such noise tends to obscure the ability to detect and measure defects in substrate 12. Also, different substrates can exhibit different amounts of reflectivity. This reflectivity variation can also obscure the ability to detect and measure defects in substrate 12. Accordingly, the circuit of FIG. 4B includes a sum amplifier 64 that generates a normalizing signal L+R at a lead 66 of a drive circuit 67. Drive circuit 67 amplifies signal L+R and provides the amplified normalizing L+R signal to an integrated circuit U2. (Drive circuit 66 has drive characteristics that match the requirements of integrated circuit U2.)

Sum circuit 64 comprises a set of switches 65. Switches 65 permit one to adjust a filter time constant exhibited by sum circuit [65] 64. This permits one to either detect or ignore stain regions of varying reflectivity on substrate 12, depending upon the setting of switches 65.

Sum circuit [66] 64 also includes an amplifier U1D for providing an output signal on a lead [68] 69. Buffer U1D provides another signal indicative of the magnitude of L+R. This signal can be used to determine when the laser beam strikes the end of substrate 12 as the laser scans across the surface.

Circuit U2 receives the amplified normalizing signal L+R and signals L and R. Circuit U2 provides a signal equal to (L−R)/(L+R) on a lead 68. Signal (L−R)/(L+R) is a measure of the extent to which a defect deflects light to the left or to the right, corrected for any change in the total strength of signals L and R caused by laser power fluctuation or changes in disk surface reflectivity.

Integrated circuit U2 also receives voltage signals ER, Y1 and Y2 from an amplifier circuit 70. Signals Y1 and Y2 permit adjustment of an amplification constant used by integrated circuit U2. (This amplification is proportional to signals Y1–Y2.) Of importance, if the gain is too high, it can cause instability in circuit U2.

Signal (L−R)/(L+R) is provided to an amplifier U3, which provides an output signal OS at an output lead 72. Output signal OS is coupled to a set of comparitors 70a, 70b, 70c and 70d, which compare signal OS to reference voltages RVa, RVb, RVc and RVd, respectively (FIG. 4C). If laser beam 16 is not deflected by a defect on substrate 12, signal OS will be less than any of voltages RVa to RVd. If laser beam 16 is slightly deflected by a defect, signal OS will exceed reference voltage Rva, and comparitor 70a will provide an active binary output signal at an output lead OL70a, while concurrently, the output of comparitors 70b–70d will be inactive. If laser beam 16 is deflected to a greater extent, signal OS will exceed reference voltage RVb, causing the binary output signal of comparitor 70b to go active. Comparitors 70c and 70d function in a similar manner. Thus, comparitors 70a to 70d provide a measure of the extent to which laser beam 16 is deflected by defects on substrate 12. (This, in turn, is a measure of the steepness of the defect walls, which is important because the steepness of the walls is a measure of the size of the defect.) The binary output signals on leads 0,70a to OL70d are coupled to latches which can be processed by circuitry similar to that used to process signals BOS421–BOS48d, described above.

FIG. 4D illustrates power supply circuitry 100 used by the circuitry of FIGS. 4A and 4B. Circuitry 100 receives input voltages of 15V and −15V, and generates therefrom output voltages of 5 volts, ground and −5 volts. Circuitry for providing such output voltages are known to those skilled in the art, and thus this circuitry will not be described in further detail.

The bi-cell photodiode 50 and associated circuitry of FIGS. 4A to 4D can be used to replace photomultiplier tubes 14a, 14b. However, in one embodiment, photomultiplier tubes 38a, 38b are used to detect wide angle scattering of light as discussed above.

FIG. 6 is a cross section view of a module 200 containing a printed circuit board 201 that carries bi-cell photodiode 50 and a portion of the circuitry of FIGS. 4A to 4D. Module 200 is mounted on a block 202 coupled to a holder 203. Module 200 includes a first mechanism 204 for making fine position adjustments of bi-cell photodiode 50 in the direction of arrow 206. Such adjustments are controlled by turning a first control screw 208. Mounted on first mechanism 204 is a second mechanism 210 for making fine position adjustments of bi-cell photodiode 50 in a direction perpendicular to arrow 206. These adjustments are controlled by turning a second control screw 214. (Control screw 214 is perpendicular to control screw 208.) A bock 212 is affixed to second mechanism 210. PC board 201 is mounted within block 212.

Bi-cell photodiode 50 is located in a central portion of PC board 201. Block 212 contains a window 218 for permitting laser 16a to strike photodiode 50. (As mentioned above, laser 16a is reflected off of the substrate being tested for defects.) Block 212 includes a first connector 220 for receiving electrical power via a wire 222 and a second 8 connector 224 for providing signal L+R. A second connector within block 212 (not shown) provides signal L−R/L+R. These signals are processed by circuitry outside of block 212 in the manner discussed above.

After a substrate is inspected with the apparatus and method of the present invention, the substrate is typically used to manufacture a magnetic disk. During this process, an underlayer, a magnetic layer, and a protective overcoat are deposited, e.g. by sputtering or evaporation, onto the substrate. A lubricant layer is then applied to the overcoat. An example of a process for completing the manufacture of a magnetic disk after substrate inspection is set forth in U.S. patent application Ser. No. 08/984,753, filed by Bertero, et al., assigned to the assignee of the present invention and incorporated herein by reference.

While the invention has been described with respect to a specific embodiment, those skilled in the art will appreciate that changes can be made in form and detail without departing from the spirit and scope of the invention. For example, different types of lasers (e.g. diode lasers or gas lasers) can be used to inspect a substrate in accordance with my invention. Further, this structure can be used to test different kinds of substrates, e.g. glass or glass ceramic substrates. Such substrates can be used to manufacture magnetic disks or other devices. Accordingly, all such changes come within the present invention.

TABLE I

| Component | Value |
|---|---|
| R1 | 3MΩ |
| R2 | 200Ω |
| R3 | 10Ω |
| R4 | 82KΩ |
| R5 | 10Ω |
| R6 | 10KΩ |
| R7 | 10KΩ |
| R8 | 100KΩ variable resistor |
| R9 | 10Ω |
| R11 | 56KΩ |
| R12 | 10KΩ |
| R13 | 10KΩ |
| R14 | 10KΩ |
| R15 | 15KΩ |
| R16 | 10KΩ |
| R17 | 15KΩ |
| R18 | 50Ω |
| R16 | 10KΩ |
| C1 | 0.1 µF |
| C2 | 0.1 µF |
| C3 | 0.1 µF |
| C4 | 4700 pF |
| C5 | 0.1 µF |
| C6 | 1500 pF |
| C7 | 0.1 µF |
| C8 | 4.7 µF |
| C9 | 0.1 µF |
| C10 | 0.1 µF |
| C11 | 4.7 µF |
| C12 | 0.1 µF |
| C13 | 1 pF |
| C14 | 0.1 µF |
| C15 | 0.1 µF |
| C16 | 0.1 µF |
| C17 | 1 pF |
| C18 | 0.1 µF |
| C19 | 0.1 µF |

| Integrated Circuit | Model | Manufacturer |
|---|---|---|
| U1A, U1B, U1C | AD713R-16 | Analog Devices |
| U2 | AD734 | Analog Devices |
| U3 | LM6321M | National Semiconductor |
| U5 | LM78L05ACZ | National Semiconductor |
| U6 | LM79L05ACZ | National Semiconductor |
| U7 | OPA655 | Burr Brown |
| U9 | OPA655 | Burr Brown |

We claim:

1. Structure for detecting defects in a workpiece comprising:

a bi-cell photosensitive device for receiving laser light reflected off of said workpiece, said bi-cell photosensitive device comprising a first cell for generating a first signal corresponding to the amount of light striking said first cell and a second cell for generating a second signal corresponding to the amount of light striking said second cell;

a circuit coupled to said bi-cell photosensitive device for generating a third signal, said third signal providing a measure of the sum of the first and second signals, said circuit providing a fourth signal which is a measure of the difference between said first and second signals normalized by said third signal, said fourth signal serving as a defect detection signal, said fourth signal providing a measure of the angle at which said light reflects off said workpiece, wherein said fourth signal is compared to a reference value to provide an indication of the slope of the sides of the defect detected by said circuit.

2. Structure of claim 1 wherein said bi-cell photosensitive device comprises two photodiodes mounted on a common substrate, said photodiodes being adjacent to one another.

3. Structure of claim 1 wherein said bi-cell photosensitive device is coupled to a bias voltage for reducing the capacitance exhibited by said bi-cell photosensitive device.

4. Structure of claim 1 wherein said bi-cell photosensitive device comprises a photodiode, said photodiode being biased with a voltage such that said voltage reduces the capacitance exhibited by said photodiode.

5. Structure of claim 4 wherein the reduction in capacitance exhibited by said photodiode increases the bandwidth of said structure.

6. Structure of claim 4 wherein the capacitance exhibited by said photodiode is less than or equal to about 13 pF.

7. Structure of claim 6 wherein the capacitance exhibited by said photodiode is between 0.1 and 13 pF.

8. Structure of claim 4 wherein the bandwidth of said circuit is greater than 100 kHz.

9. Structure of claim 1 further comprising a source of a laser beam, said laser beam reflecting off said workpiece and striking said bi-cell photosensitive device.

10. Structure of claim 1 wherein said structure is capable of detecting defects on a substrate having a wall slope less than about 0.02°.

11. Structure for detecting defects in a workpiece comprising:

a bi-cell photosensitive device for receiving laser light reflected off of said workpiece, said bi-cell photosensitive device comprising a first cell for generating a first signal corresponding to the amount of light striking said first cell and a second cell for generating a second signal corresponding to the amount of light striking said second cell;

a circuit coupled to said bi-cell photosensitive device for generating a third signal, said third signal providing a measure of the sum of the first and second signals, said circuit providing a fourth signal which is a measure of the difference between said first and second signals normalized by said third signal, said fourth signal serving as a defect detection signal, said fourth signal providing a measure of the angle at which said light reflects off said workpiece, wherein said fourth signal is coupled to a set of comparators, each comparator comparing said fourth signal to a different reference voltage, said comparators providing output signals, each output signal indicating whether the slope of the defect detected exceeds a certain value so that characteristics of the defect detected by said apparatus can be ascertained.

12. Structure for detecting defects in a workpiece comprising:

a bi-cell photosensitive device for receiving laser light reflected off of said workpiece, said bi-cell photosensitive device comprising a first cell for generating a first signal corresponding to the amount of light striking said first cell and a second cell for generating a second signal corresponding to the amount of light striking said second cell;

a circuit coupled to said bi-cell photosensitive device for generating a third signal, said third signal providing a measure of the sum of the first and second signals, said circuit providing a fourth signal which is a measure of the difference between said first and second signals normalized by said third signal, said fourth signal serving as a defect detection signal, said fourth signal providing a measure of the angle at which said light reflects off said workpiece, wherein said bi-cell photosensitive device comprises a photodiode, said photodiode being biased with a voltage, whereby said voltage reduces the capacitance exhibited by said photodiode, and wherein the portion of said circuit which generates said third signal comprises a filter characterized by a time constant, said time constant being adjustable so that said circuit can optionally either detect or ignore stain regions on said workpiece.

13. Structure for detecting defects in a workpiece comprising:

a bi-cell photosensitive device for receiving laser light reflected off of said workpiece, said bi-cell photosensitive device comprising a first cell for generating a first signal corresponding to the amount of light striking said first cell and a second cell for generating a second signal corresponding to the amount of light striking said second cell;

a circuit coupled to said bi-cell photosensitive device for generating a third signal, said third signal providing a measure of the sum of the first and second signals, said circuit providing a fourth signal which is a measure of the difference between said first and second signals normalized by said third signal, said fourth signal serving as a defect detection signal, said fourth signal providing a measure of the angle at which said light reflects off said workpiece, wherein said structure inspects substrates used in the manufacture of magnetic disks.

14. Method comprising:

reflecting a laser off of a workpiece so that said laser strikes a bi-cell photodetector, said bi-cell photodetector comprising first and second cells, said photodetector providing a first signal indicative of the amount of light striking said first cell and a second signal indicative of the amount of light striking said second cell; and providing a third signal providing a measure of (L−R)/(L+R), where L is the first signal, and R is the second signal, said third signal providing a measure of the angle at which said light reflects off of said workpiece to thereby provide a measure of the characteristics of a defect in said workpiece; and comparing said third signal to a reference value to determine whether said third signal exceeds said reference value.

15. Method of claim 14 further comprising biasing said photodetector to reduce the capacitance of said photodetector.

16. Method of claim 15 wherein said biasing of said photodetector comprises applying a voltage to said photodetector so that it exhibits a capacitance less than or equal to about 13 pF, and can provide a signal having a bandwidth greater than 100 kHz.

17. Method of claim 14 wherein said providing of said third signal is performed using a circuit that generates a fourth signal that is a measure of L+R, said method further comprising adjusting said circuit to either detect or ignore stained regions of said workpiece.

18. Method comprising:
reflecting a laser off of a workpiece so that said laser strikes a bi-cell photodetector, said bi-cell photodetector comprising first and second cells, said photodetector providing a first signal indicative of the amount of light striking said first cell and a second signal indicative of the amount of light striking said second cell; and
providing a third signal providing a measure of (L−R)/(L+R), where L is the first signal, and R is the second signal, said third signal providing a measure of the angle at which said light reflects off of said workpiece to thereby provide a measure of the characteristics of a defect in said workpiece, wherein said workpiece is a substrate used to manufacture a magnetic disk.

19. Method of claim 18 further comprising forming a magnetic layer over said substrate, said magnetic layer constituting a magnetic data recording layer for said magnetic disk.

20. Method of claim 14 wherein said defect has a wall slope less than about 0.02°.

21. Structure comprising:
a light source for providing light that reflects off of a workpiece;
a photodetector receiving said reflected light, said photodetector comprising first and second cells, said photodetector providing a first signal indicative of the amount of light striking said first cell and a second signal indicative of the amount of light striking said second cell;
a circuit providing an output signal which is a measure of L−R, where L is the first signal, and R is the second signal, said output signal providing a measure of the angle at which said light reflects off of said workpiece; and
a comparator for comparing said output signal to a reference value to thereby detect defects in said workpiece.

22. Structure of claim 21 wherein said first and second cells are formed on a common substrate.

23. Structure comprising:
a light source for providing light that reflects off of a workpiece;
a photodetector receiving said reflected light, said photodetector comprising first and second cells, said photodetector providing a first signal indicative of the amount of light striking said first cell and a second signal indicative of the amount of light striking said second cell; and
a circuit providing an output signal which is a measure of (L−R)/(L+R), where L is the first signal, and R is the second signal, said output signal providing a measure of the angle at which said light reflects off of said workpiece; and
a comparator for comparing said output signal to a reference value to thereby detect defects in said workpiece.

24. Structure comprising:
a laser source for providing a laser beam that reflects off of a workpiece;
a photodetector receiving said reflected laser beam, said photodetector comprising first and second cells, said photodetector providing a first signal indicative of the amount of said laser beam striking said first cell and a second signal indicative of the amount of said laser beam striking said second cell; and
a circuit providing an output signal which is a measure of L−R, where L is the first signal, and R is the second signal, said output signal providing a measure of the angle at which said laser beam reflects off of said workpiece; and
a comparator for comparing said output signal to a reference value to thereby detect defects in said workpiece.

25. Structure comprising:
a laser source for providing a laser beam that reflects off of a workpiece;
a photodetector receiving said reflected laser beam, said photodetector comprising first and second cells, said photodetector providing a first signal indicative of the amount of said laser beam striking said first cell and a second signal indicative of the amount of laser beam striking said second cell; and
a circuit providing an output signal which is a measure of (L−R)/(L+R), where L is the first signal, and R is the second signal, said output signal providing a measure of the angle at which said laser beam reflects off of said workpiece; and
a comparator for comparing said output signal to a reference value to thereby detect defects in said workpiece.

26. Method for detecting defects in a workpiece comprising:
reflecting light off of a workpiece so that the reflected light strikes a photosensitive device, said photosensitive device comprising a first cell for generating a first signal corresponding to the amount of light striking said first cell and a second cell for generating a second signal corresponding to the amount of light striking said second cell;
generating a third signal, said third signal providing a measure of the difference between the first and second signals, said third signal providing a measure of the angle at which said light reflects off said workpiece; and
comparing said third signal to a reference value to thereby detect defects in said workpiece.

27. Method of claim 26 wherein said first and second cells are formed on a common substrate.

28. Method for detecting defects in a workpiece comprising:
reflecting light off of a workpiece so that the reflected light strikes a photosensitive device, said photosensitive device comprising a first cell for generating a first signal corresponding to the amount of light striking said first cell and a second cell for generating a second signal corresponding to the amount of light striking said second cell;
generating a third signal, said third signal providing a measure of the difference between the first and second signals normalized by the sum of the first and second signals, said third signal providing a measure of the angle at which said light reflects off said workpiece; and comparing said third signal to a reference value to thereby detect defects in said workpiece.

29. Method for detecting defects in a workpiece comprising:

reflecting a laser beam off of a workpiece so that the reflected laser beam strikes a photosensitive device, said photosensitive device comprising a first cell for generating a first signal corresponding to the amount of said laser beam striking said first cell and a second cell for generating a second signal corresponding to the amount of said laser beam striking said second cell;

generating a third signal, said third signal providing a measure of the difference between the first and second signals, said third signal providing a measure of the angle at which said laser beam reflects off said workpiece; and comparing said third signal to a reference value to thereby detect defects in said workpiece.

30. Method for detecting defects in a workpiece comprising:

reflecting a laser beam off of a workpiece so that the reflected laser beam strikes a photosensitive device, said photosensitive device comprising a first cell for generating a first signal corresponding to the amount of said laser beam striking said first cell and a second cell for generating a second signal corresponding to the amount of said laser beam striking said second cell;

generating a third signal, said third signal providing a measure of the difference between the first and second signals normalized by the sum of the first and second signals, said third signal providing a measure of the angle at which said laser beam reflects off said workpiece; and comparing said third signal to a reference value to thereby detect defects in said workpiece.

* * * * *